(12) United States Patent
Reddy et al.

(10) Patent No.: US 9,950,983 B2
(45) Date of Patent: Apr. 24, 2018

(54) TRICYCLIC COMPOUNDS AND PROCESS FOR PREPARATION THEREOF

(71) Applicant: Council of Scientific and Industrial Research, New Delhi (IN)

(72) Inventors: Dumbala Srinivasa Reddy, Pune (IN); Kishor Laxman Handore, Pune (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 15/328,425

(22) PCT Filed: Jul. 23, 2015

(86) PCT No.: PCT/IN2015/050074
§ 371 (c)(1),
(2) Date: Jan. 23, 2017

(87) PCT Pub. No.: WO2016/013032
PCT Pub. Date: Jan. 28, 2016

(65) Prior Publication Data
US 2017/0233324 A1 Aug. 17, 2017

(30) Foreign Application Priority Data

Jul. 23, 2014 (IN) .......................... 2082/DEL/2014

(51) Int. Cl.
C07C 49/00 (2006.01)
A01N 35/06 (2006.01)
C07C 49/643 (2006.01)

(52) U.S. Cl.
CPC ............ *C07C 49/643* (2013.01); *A01N 35/06* (2013.01); *C07C 2603/08* (2017.05); *C07C 2603/12* (2017.05)

(58) Field of Classification Search
CPC .... C07C 49/643; C07C 2603/10; A01N 35/06
USPC ...................................................... 568/373
See application file for complete search history.

(56) References Cited

FOREIGN PATENT DOCUMENTS

WO WO-2016013032 1/2016
WO WO-2016013032 A4 1/2016

OTHER PUBLICATIONS

Handore, Kishor L., et al., "Ready Access to Functionally Embellished cis-Hydrindanes and cis- Decalins: Protecting Group-Free Total Syntheses of (±)-Nootkatone and (±)-Noreremophilane", J. Org. Chem. 2013, 78, 8149-8154, (Jul. 15, 2013), 8149-8154.

Moser, William H., et al., "Photoreactions of gamma, delta-Unsaturated Chromium Carbene Complexes", J. Am. Chem. Soc., 1996, 118 (34), pp. 7873-7880, (Aug. 28, 1996), 7873-7880.

Qian, Shan, et al., "Enantioselective total synthesis of (+)-sarcandralactone", Tetrahedron, vol. 69, Issue 52, Dec. 30, 2013, pp. 11169-11173, (Dec. 30, 2013), 11169-11173.

Reddy, D. Srinivasa, et al., "A General Approach Toward Bakkanes: Short Synthesis of (±)-bakkenolide-A (Fukinanolide)", Organic Letters, vol. 6, No. 19, 3345-3347 (2004), (Aug. 19, 2004), 3345-3347.

Yue, Guizhou, et al., "Total syntheses of lindenane-type sesquiterpenoids: (±)-chloranthalactones A, B, F, (±)-9-hydroxy heterogorgiolide, and (±)-shizukanolide E", Tetrahedron, vol. 68, Issue 47, Nov. 25, 2012, pp. 9624-9637, (Nov. 25, 2012), 9624-9637.

Zhu, Betty C.R., et al., "Nootkatone is a Repellent for Formosan Subterranean Termite (*Coptotermes formosanus*)", Journal of Chemical Ecology, vol. 27, No. 3, 2001, (2001), 523-531.

"International Application No. PCT/IN2015/050074, Article 19 Amendments and Remarks filed Jan. 29, 2016", (dated Jan. 29, 2016), 9 pgs.

"International Application No. PCT/IN2015/050074, International Search Report and Written Opinion dated Nov. 30, 2015", (dated Nov. 30, 2015), 9 pgs.

Kutney, James P., et al., "The chemistry of thujone. XV. A versatile route to antifeedants of the polygodial family", Canadian Journal of Chemistry, 1990, 68(10): 1698-1708, (1990), 1698-1708.

Kutney, James P., et al., "The chemistry of thujone. XVII. The synthesis of ambergris fragrances and related analogues", Canadian Journal of Chemistry, 1994, 72(6): 1570-1581, (Jan. 1, 1994), 1570-1581.

*Primary Examiner* — Sikarl A Witherspoon
(74) *Attorney, Agent, or Firm* — Schwegman Lundberg & Woessner, P.A.

(57) ABSTRACT

The present invention discloses tricyclic compounds of formula (I) or salt thereof and their process for synthesis. Further, the present invention relates to the use of these novel tricyclic compounds of formula (I) or salt thereof as insect repellents.

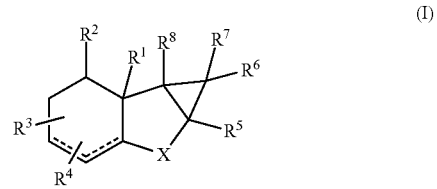

(I)

9 Claims, 2 Drawing Sheets

TRICYCLIC COMPOUNDS AND PROCESS FOR PREPARATION THEREOF

PRIORITY CLAIM TO RELATED APPLICATIONS

This application is a U.S. national stage application filed under 35 U.S.C. § 371 from International Application Serial No. PCT/IN2015/050074, which was filed 23 Jul. 2015, and published as WO2016/013032 on 28 Jan. 2016, and which claims priority to Indian Application No. 2082/DEL/2014, filed 23 Jul. 2014, which applications and publication are incorporated by reference as if reproduced herein and made a part hereof in their entirety, and the benefit of priority of each of which is claimed herein.

FIELD OF THE INVENTION

The present invention relates to tricyclic compounds of formula (I) or salt thereof. Particularly, the present invention relates to process for synthesis of tricyclic compounds of formula (I) or salt thereof. More particularly, the present invention relates to the use of these tricyclic compounds of formula (I) or salt thereof as insect repellents.

BACKGROUND OF THE INVENTION

Nardoaristolones B is a terpenoid derived from aristolane-type sesquiterpenoid. Nardoaristolones B possesses a nor-aristolone sesquiterpenoid skeleton with an unusual 3/4/5 tricyclic ring system.

Repellent substances generally cause insects to be driven away from, or to reject, otherwise insect-acceptable food sources or habitats. Most known repellents are only mildly toxic. A few of the known repellents, in fact, are not active poisons at all but rather prevent damage to plants/animals or articles of manufacture by making insect food sources or living conditions unattractive or offensive. Most current commercial insect repellents contain the synthetic chemical N,N-diethyl-m-toluamide (DEET) as their primary active ingredient. For instance, repellents sold under the major commercial brand names such as Off!®, Deep Woods Off!®, and Cutter® are all DEET based products and comprise 85% of insect repellent sales (Consumer Reports Buying Guide, 1994 Special Year-End Issue).

Article titled "Nootkatone is a repellent for Formosan subterranean termite (*Coptotermes formosanus*)." By BC Zhu et al. published in *J Chem Ecol.*, 2001; 27(3); 523-31 first time reports nootkatone, a sesquiterpene ketone, isolated from vetiver oil as a strong repellent and toxicant to Formosan subterranean termites. The lowest effective concentration tested was 10 micrograms/g substrate.

Article titled "A General Approach toward Bakkanes: Short Synthesis of (±)-Bakkenolide-A (Fukinanolide)" by DS Reddy published in *Org. Lett.*, 2004, 6 (19), pp 3345-3347 reports an efficient, general, and fully stereo controlled approach to the family of bakkanes. This route highlights a highly diastereoselective Diels-Alder/aldol sequence to furnish the common hydrindane precursor for the synthesis of bakkanes Article titled "Ready Access to Functionally Embellished cis-Hydrindanes and cis-Decalins: Protecting Group-Free Total Syntheses of (±)-Nootkatone and (±)-Noreremophilane" by KL Handore et al. published in J. Org. Chem., 2013, 78 (16), pp 8149-8154 reports a simple and efficient synthesis of functionalized cis-hydrindanes and cis-decalins achieved using a sequential Diels-Alder/aldol approach in a highly diastereoselective manner. The article reports ready access to 13 new cis-hydrindanes/cis-decalins, a protecting group-free total synthesis of an insect repellent Nootkatone, and the first synthesis of a Noreremophilane using the shortest sequence.

As the existing repellents are developing resistance and have side effects. Hence, there is a need to identify and develop novel insect repellents to control the spread of various tropical diseases.

OBJECTIVE OF THE INVENTION

The main objective of present invention is to provide a tricyclic compound of formula (I) or salt thereof.

Another objective of present invention is to provide a process for the synthesis of tricyclic compound of formula (I).

Yet another object of present invention is to provide use of tricyclic compound of formula (I) or salt thereof as insect repellent.

SUMMARY OF THE INVENTION

Figure 1:
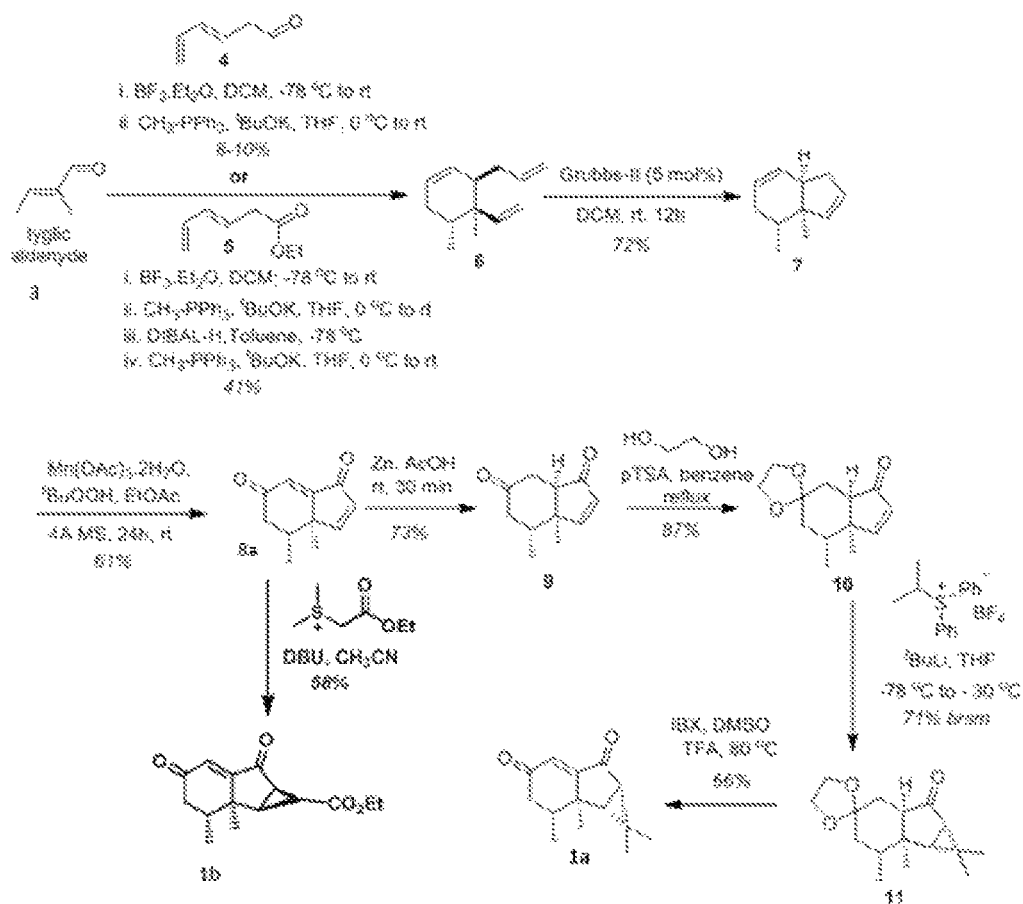
FIG. 1 represents process steps for the synthesis of 3/5/6 tricyclic compounds of formula (I).

Accordingly, present invention provides a compound of formula (I)

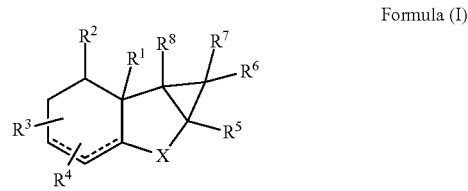

Formula (I)

wherein,
$R^1$, $R^2$, $R^3$, $R^4$, $R^5$, $R^6$, $R^7$, $R^8$ is selected from group consisting of hydrogen, alkyl ($C_1$ to $C_4$), COOR, COOH COR, CONRR, $CH_2OR$, NRR wherein, any two of $R^1$, $R^2$, $R^3$, $R^4$, $R^5$, $R^6$, $R^7$, $R^8$ may form a 3 to 8 membered carbocyclic ring which may optionally be substituted or may contain a heteroatom selected from O or N;
X is selected from C=O; C=S or C—R—R;
R is selected from hydrogen, alkyl ($C_1$ to $C_4$);
wherein any two R may form a 3 to 8 membered carbocyclic ring which may optionally be substituted or may contain a heteroatom selected from O or N;
'........' represents a single or double bond;
either of the ring in formula (I) may additionally contain at least one carbonyl group or salt thereof.

In an embodiment of the present invention, the said compounds are selected from the group consisting of:
i. (1aR,1bR,2R,6aS)-1,1,1b,2-Tetramethyl-1,1a,1b,2,3,6a-hexahydrocyclopropa[a]indene-4,6-dione (1a),
ii. Ethyl(1R,1aS,1bR,2R,6aR)-1b,2-dimethyl-4,6-dioxo-1, 1a,1b,2,3,4,6,6a-octahydrocyclopropa[a]indene-1-carboxylate (1b), iii. (1aR,6aR)-1,1-Dimethyl-1a,1b,2,3,6,6a-hexahydrocyclopropa[a]-inden-4(1H)-one (1c),
iv. (1aR,6aR)-1,1,5-trimethyl-1a,1b,2,3,6,6a hexahydrocyclopropa[a]inden-4(1H)-one (1d),
v. (1aR,1bS,6aR)-1,1,2-Trimethyl-1a,1b,2,3,6,6a-hexahydrocyclo propa[a]inden-4(1H)-one (1e),
vi. (1aR,1bS,6aR)-2-Ethyl-1,1-dimethyl-1a,1b,2,3,6,6a-hexahydrocyclo propa[a]inden-4(1H)-one (1f),
vii. (1aR,1bS,6aR)-1,1-Dimethyl-2-propyl-1a,1b,2,3,6,6a-hexahydrocyclo propa[a]inden-4(1H)-one (1g),
viii. (1aR,1bR,6aR)-1,1,2,2-Tetramethyl-1a,1b,2,3,6,6a-hexahydrocyclopropa[a]inden-4(1H)-one (1h).

In another embodiment, present invention provides a process for the preparation of compound of formula (I) comprising the steps of:

a) adding boron trifluoride diethyl etherate ($BF_3 \cdot OEt_2$) to a solution of diene compounds of formula 4 and (E)-2-methylbut-2-enal of formula 3 in Dichloromethane ($CH_2Cl_2$) followed by stirring the reaction for the period ranging from 10 to 12 h at temperature in the range of −78° C. to 30° C. to afford compound of formula 6; or
b) adding Grubbs second-generation catalyst to a solution of compound of formula 6 of step (a) followed by stirring the mixture for 22 to 24 h temperature in the range of 25 to 30° C. to afford compound of formula 7;
c) adding Manganese triacetate dehydrate [Mn(OAC)$_3 \cdot 2H_2O$] and tert-butyl hydroperoxide ($^t$-BuOOH) to a solution of compound of formula 7 of step (b) in ethyl acetate (EtOAc) followed by stirring the reaction mixture for 22 to 24 h at temperature 25 to 30° C. to give compound of formula 8a;
d) adding 1,8-Diazabicyclo[5.4.0]undec-7-ene (DBU) to a suspension of (ethoxycarbonylmethyl)-dimethylsulfonium bromide in chloroform ($CHCl_3$) to obtain a mixture followed by addition of solution of compound of formula 8a of step (c) in $CHCl_3$ and stirring the reaction mixture to afford compound of formula 1b;
e) adding zinc dust to a stirred solution of dienedione of formula 8a of step (c) in acetic acid followed by stirring for 20 to 30 min at temperature in the range of 25 to 30° C. to afford enone compound of formula 9;
f) adding ethylene glycol and p-Toluenesulfonic acid (PTSA) to a solution of compound of formula 9 of step (e) in benzene followed by refluxing for 50 to 60 minutes at temperature in the range of 80 to 85° C. to afford compound of formula 10;
g) adding the solution of $^t$-BuLi in pentane and isopropyldiphenylsulfonium tetrafluoroborate in THF to a solution of compound of formula 10 of step (f) followed by cooling the reaction mixture to (−)15 to (−)20° C. for 50 to 60 minutes quenching the reaction mixture to give compound of formula 11;
h) adding 2-iodoxybenzoic acid (IBX) and trifluoroacetic acid (TFA) to a solution of ketone of formula 11 of step (f) in dimethyl sulfoxide (DMSO) followed by stirring the reaction mixture at 70 to 80° C. for 20 to 24 h to afford compound of formula (I).

In still another embodiment of the present invention, the step (c) is carried out under nitrogen atmosphere.

In yet another embodiment of the present invention, compound 6 of the step (a) may optionally be prepared by the process comprising the steps of:

a. adding $BF_3 \cdot OEt_2$ to a solution of diene of formula 5 and (E)-2-methylbut-2-enal of formula 3 in $CH_2Cl_2$ followed by stirring the reaction mixture at 25° C. for 12 hrs to afford aldehyde S-I;

b. adding methyl triphenylphosphonium bromide in tetrahydrofuran (THF) and potassium tert-butoxide to aldehyde S-I of step (a) followed by stirring at 0° C. for 1 h to afford ester S-II;
c. adding diisobutylaluminium hydride (DIBAL) in toluene to a solution of compounds of step (b) in toluene at −78° C. with constant stirring to afford compound of formula aldehyde S-III;
d. Adding methyl triphenylphosphonium bromide in tetrahydrofuran (THF) and potassium tert-butoxide to aldehyde S-I of step (a) followed by stirring at 0° C. for 1 h to afford 6.

In yet another embodiment of the present invention, the process further comprises adding a solution of tert-Butyllithium ($^t$-BuLi) in pentane and isopropyldiphenylsulfonium tetrafluoroborate in THF to a solution of compound of formula 8a of step (c) followed by cooling the mixture to −30° C. for 1 h to afford Nardoaristolone B.

In yet another embodiment, present invention provides a process for the preparation of compound of formula (I) comprises adding potassium tert-butoxide (KO$^t$Bu) and ketone compound to a stirred solution of compound of formula 14 ((1R,5S)-6,6-dimethylbicyclo[3.1.0]hexan-3-one) and sodium sulfate ($Na_2SO_4$) in tertiary butanol followed by stirring the reaction mixture for the period ranging from 0.5 h 6 h at temperature 25° C.-60° C. to afford compounds of formula (I).

In yet another embodiment, present invention provides a process for the preparation of compounds of formula (I), wherein ketone compounds is selected from methyl vinyl ketone, pent-1-en-3-one, (E)-pent-3-en-2-one, (E)-hex-3-en-2-one, (E)-hept-3-en-2-one, 4-methylpent-3-en-2-one.

In yet another embodiment of the present invention, the compounds of formula (I) are useful as insect repellents.

In yet another embodiment of the present invention, the protection period of the compounds of formula (I) against mosquito bites is in the range of 1.23 h to 6.46 h at the concentration in the range of 0.25 to 0.50 mg/cm$^2$.

DETAILED DESCRIPTION OF THE INVENTION

The present invention provides tricyclic compounds of formula (I) and process of synthesis thereof which are useful as insect repellents.

The present invention provides 3/5/6 tricyclic compounds of formula (I),

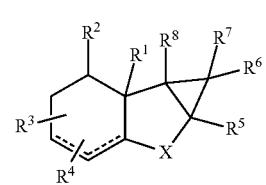

Formula (I)

wherein,
$R^1$, $R^2$, $R^3$, $R^4$, $R^5$, $R^6$, $R^7$, $R^8$ is selected from the group consisting of hydrogen, alkyl ($C_1$-$C_4$), COOR, COOH, COR, CONRR, CH$_2$OR, NRR;
wherein any two of $R^1$, $R^2$, $R^3$, $R^4$, $R^5$, $R^6$, $R^7$, $R^8$ may form a 3 to 8 membered carbocyclic ring which may optionally be substituted or may contain a heteroatom selected from O or N;

X is selected from C=O; C=S or CRR;
R is selected from hydrogen, alkyl (C$_1$-C$_4$);
wherein any two R may form a 3 to 8 membered carbocyclic ring which may optionally be substituted or may contain a heteroatom selected from O or N;
'........' represents a single or double bond;
Either of the ring in formula (I) may additionally contain at least one carbonyl group or salt thereof.

The tricyclic compounds of formula (I) are selected from the group consisting of:
(1aR,1bR,2R,6aS)-1,1,1b,2-Tetramethyl-1,1a,1b,2,3,6a-hexahydro-cyclopropa[a]indene-4,6-dione (1a),
Ethyl(1R,1aS,1bR,2R,6aR)-1b,2-dimethyl-4,6-dioxo-1,1a,1b,2,3,4,6,6a-octahydrocyclopropa[a]indene-1-carboxylate (1b),
(1aR,6aR)-1,1-Dimethyl-1a,1b,2,3,6,6a-hexahydrocyclopropa[a]-inden-4(1H)-one (1c),
(1aR,6aR)-1,1,5-trimethyl-1a,1b,2,3,6,6a hexahydrocyclopropa[a]inden-4(1H)-one (1d),
(1aR,1bS,6aR)-1,1,2-Trimethyl-1a,1b,2,3,6,6a-hexahydrocyclo propa[a]inden-4(1H)-one (1e),
(1aR,1bS,6aR)-2-Ethyl-1,1-dimethyl-1a,1b,2,3,6,6a-hexahydrocyclo propa[a]inden-4(1H)-one (1f),
(1aR,1bS,6aR)-1,1-Dimethyl-2-propyl-1a,1b,2,3,6,6a-hexahydrocyclo propa[a]inden-4(1H)-one (1g),
(1aR,1bR,6aR)-1,1,2,2-Tetramethyl-1a,1b,2,3,6,6a-hexahydro cyclo propa[a]inden-4(1H)-one (1h).

The present invention provides a process for the synthesis of 3/5/6 tricyclic compounds formula (I) from tiglic aldehyde comprising the steps of:
a) adding boron trifluoride diethyl etherate (BF$_3$.OEt$_2$) to a solution of diene compounds of formula 4 and (E)-2-methylbut-2-enal of formula 3 in Dichloromethane (CH$_2$Cl$_2$) to afford compound of formula 6; or
Adding BF$_3$.OEt$_2$ to a solution of diene of formula 5 and (E)-2-methylbut-2-enal of formula 3 in CH$_2$Cl$_2$ followed by addition of methyl triphenylphosphonium bromide in dry tetrahydrofuran (THF) and potassium tert-butoxide to the reaction mixture followed by addition of diisobutylaluminium hydride (DIBAL-H) to afford compound of formula 6;
b) adding Grubbs second-generation catalyst to a solution of compound of formula 6 of step (a) to afford compound of formula 7;
c) Adding Manganese triacetate dehydrate [Mn(OAC)$_3$.2H$_2$O] and tert-butyl hydroperoxide ($^t$-BuOOH) to a solution of compound of formula 7 of step (b) in ethyl acetate (EtOAc) followed by stirring the reaction mixture to give compound of formula 8a;
d) adding 1,8-Diazabicyclo[5.4.0]undec-7-ene (DBU) to a suspension of (ethoxycarbonylmethyl)-dimethylsulfonium bromide in chloroform (CHCl$_3$) to obtain a mixture followed by addition of solution of compound of formula 8a of step (c) in CHCl$_3$ and stirring the reaction mixture to give compound of formula 1b;
e) adding zinc dust to a stirred solution of dienedione of formula 8a of step (c) in acetic acid to give compound of formula 9;
f) adding ethylene glycol and p-Toluenesulfonic acid (PTSA) to a solution of compound of formula 9 of step (d) followed by refluxing and quenching to give compound of formula 10;
g) adding the solution of $^t$-BuLi in pentane and isopropyldiphenylsulfonium tetrafluoroborate in THF to a solution of compound of formula 10 of step (e) and quenching the reaction mixture to give compound of formula 11;
h) adding 2-iodoxybenzoic acid (IBX) and TFA to a solution of ketone of formula 11 of step (f) in dimethyl sulfoxide (DMSO) and stirring the reaction mixture followed by quenching to give compound of formula (I).

The above process for the synthesis of 3/5/6 tricyclic compounds of formula (I) is shown in FIG. 1.

The present invention provides the process for synthesis of 3/5/6 tricyclic compounds of formula (I) from compound of formula 14

14 comprising the steps of:
a) adding potassium tert-butoxide (KO$^t$Bu) and ketone compound to a stirred solution of compound of formula 14 and sodium sulfate (Na$_2$SO$_4$) in dry tertiary butanol to obtain the reaction mixture;
b) stirring the reaction mixture for the period ranging from 0.5 h 6 h at temperature 25° C.-60° C. followed by quenching to give compound of formula (I).
c) The ketone compound is selected from methyl vinyl ketone, pent-1-en-3-one, (E)-pent-3-en-2-one, (E)-hex-3-en-2-one, (E)-hept-3-en-2-one, 4-methylpent-3-en-2-one.

Figure 2:
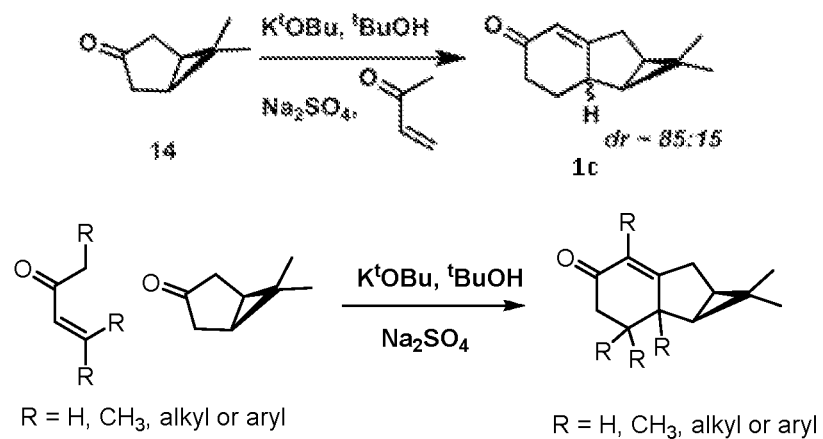
FIG. 2 represents process steps for synthesis of 3/5/6 tricyclic compounds of formula (I) from compound of formula 14.

The above process for synthesis of 3/5/6 tricyclic compounds is as shown in FIG. 2.

The present invention provides a process for the synthesis of Nardoaristolone B comprising the steps of:
a) Adding boron trifluoride diethyl etherate (BF$_3$.OEt$_2$) to a solution of diene compounds of formula 4 and (E)-2-methylbut-2-enal of formula 3 in dry CH$_2$Cl$_2$ to give compound of formula 6; or
b) Adding BF$_3$.OEt$_2$ to a solution of diene of formula 5 and (E)-2-methylbut-2-enal of formula 3 in dry Dichloromethane (CH$_2$Cl$_2$) followed by addition of suspension of methyl triphenylphosphonium bromide in dry THF and potassium tert-butoxide to the reaction mixture followed by addition of Diisobutylaluminium hydride (DIBAL) to give compound of formula 6;
c) Adding Grubbs' second-generation catalyst to a solution of compound of formula 6 of step (a) to give compound of formula 7;
d) Adding molecular sieves, Manganese triacetate dehydrate [Mn(OAC)$_3$.2H$_2$O] and tert-butyl hydroperoxide ($^t$-BuOOH) to a solution of compound of formula 7 of step (b) in ethyl acetate (EtOAc) followed by stirring the reaction mixture to give compound of formula 8a;
e) Adding a solution of tert-Butyllithium ($^t$-BuLi) in pentane and isopropyldiphenylsulfonium tetrafluoroborate in THF to a solution of compound of formula 8a and quenching the resulting mixture to give desired product Nardoaristolone B.

Figure 3:
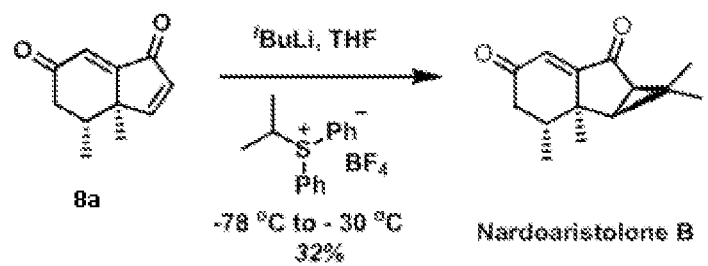
FIG. 3 represents process steps for the synthesis of Nardoaristolone B.

The above process is shown in FIG. 3.

The tricyclic compounds of present invention are used as insect repellents.

EXAMPLES

Following examples are given by way of illustration and therefore should not be construed to limit the scope of the invention.

Example 1

1a) Synthesis of (3R,4S,5R)-3-allyl-4,5-dimethyl-4-vinylcyclohex-1-ene (6)

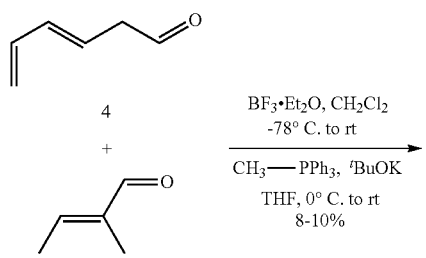

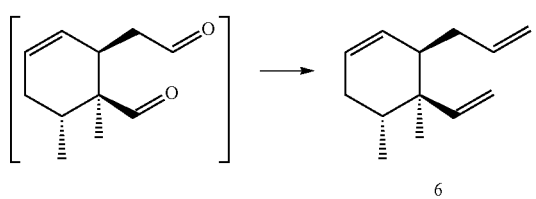

To a solution of diene 4 (100 mg, 0.892 mmol) and (E)-2-methylbut-2-enal (0.18 mL, 1.78 mmol) in dry CH$_2$Cl$_2$ (20 mL) was added BF$_3$.OEt$_2$ (0.16 mL, 0.16 mmol) dropwise at −78° C. The mixture was allowed to warm to 25° C. and was stirred for 10 h at same temperature. The CH$_2$Cl$_2$ layer was washed with saturated NaHCO$_3$ (3×10 mL) followed by H$_2$O (5 mL) and brine (5 mL), dried over Na$_2$SO$_4$, filtered and concentrated in vacuo. The crude material obtained after the removal of solvent was immediately used for next step. To a suspension of methyl triphenylphosphonium bromide (640 mg, 1.78 mmol) in dry THF (10 mL) was added potassium tert-butoxide (200 mg, 1.78 mmol) at 0° C. After 30 minutes, the solution became canary yellow color, to that above crude bis-aldehyde in THF (10 mL) was added and allowed to stir at 0° C. for 1 h. The reaction was quenched with NH$_4$Cl (5.0 ml) and extracted with petroleum ether (2×30 mL). Combined organic layer was washed with water (15 mL), brine (15 mL), dried over Na$_2$SO$_4$, filtered and concentrated in vacuo. Purification by column chromatography (silica gel 100-200, petroleum ether) afforded 6 (15 mg, 10%) as colorless oil. $^1$H NMR (400 MHz, CDCl$_3$) δ 6.01-5.94 (m, 1H), 5.86-5.77 (m, 1H), 5.62-5.61 (m, 2H), 5.05-4.99 (m, 4H), 2.31-2.19 (m, 2H), 1.91-1.84 (m, 2H), 1.72-1.64 (m, 2H), 1.03 (s, 3H), 0.86 (d, J=6.8 Hz, 3H); $^{13}$C NMR (100 MHz, CDCl$_3$) δ 146.1, 138.3, 129.1, 125.1, 115.7, 112.3, 43.9, 40.9, 35.8, 35.1, 31.6, 19.3, 16.4; HRMS (ESI) calcd for C$_{13}$H$_{20}$ [M−H] 175.1481, found 175.1480.

1b) Synthesis of Ethyl 2-((1R,5R,6S)-6-formyl-5,6-dimethylcyclohex-2-en-1-yl) acetate (S-I)

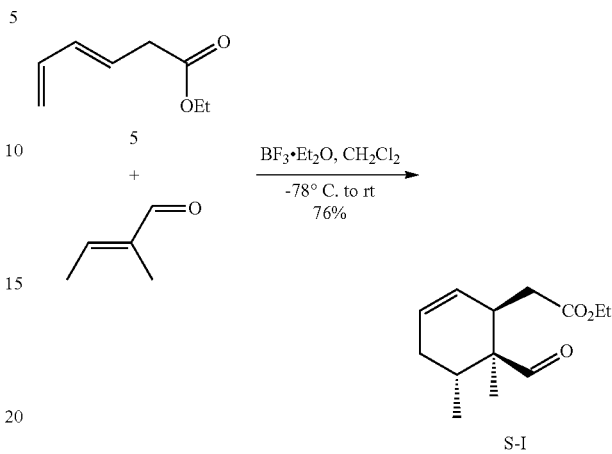

To a solution of diene 5 (6.0 g, 0.042 mol) and (E)-2-methylbut-2-enal (10.3 mL, 0.107 mmol) in dry CH$_2$Cl$_2$ (200 mL) was added BF$_3$.OEt$_2$ (10.6 mL, 0.085 mol) dropwise at −78° C. The mixture was allowed to warm to 25° C. and was stirred for 12 h at same temperature. The CH$_2$Cl$_2$ layer was washed with saturated NaHCO$_3$ (3×50 mL) followed by H$_2$O (50 mL) and brine (50 mL), dried over Na$_2$SO$_4$, filtered and concentrated in vacuo. The crude material obtained after the removal of solvent was purified by column chromatography (silica gel 100-200, 1.0:9.0 ethyl acetate:petroleum ether) to afford S-I (7.3 g, 76%) as light yellow oil. IR (neat, cm$^{-1}$) 2978, 1732, 1174; $^1$H NMR (400 MHz, CDCl$_3$) δ=9.60 (s, 1H), 5.71-5.66 (m, 1H), 5.64-5.97 (m 1H), 4.13 (q, J=7.2 Hz, 2H), 2.65-2.59 (m, 1H), 2.45 (dd, J=5.4 Hz, 15.8 Hz, 1H), 2.37-2.30 (m, 1H), 2.25-2.18 (m, 1H), 2.17-2.05 (m, 1H), 1.79-1.72 (m, 1H), 1.25 (t, J=7.2 Hz, 3H), 1.08 (s, 3H), 0.93 (d, J=6.8 Hz, 3H); $^{13}$C NMR (100 MHz, CDCl$_3$) δ=206.6, 172.6, 127.4, 126.1, 60.4, 49.6, 37.6, 35.6, 30.65, 29.5, 15.7, 15.6, 13.9;

1c) Synthesis of Ethyl 2-((1R,5R,6S)-5,6-dimethyl-6-vinylcyclohex-2-en-1-yl) acetate (S-II)

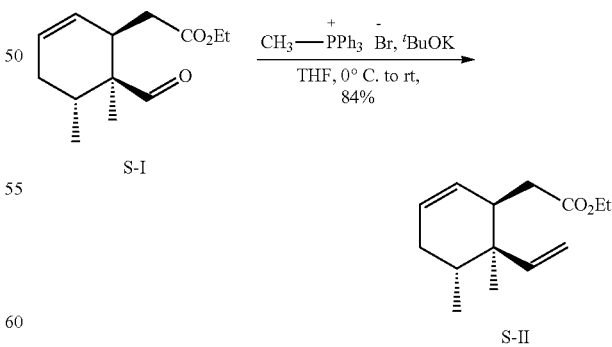

To a suspension of methyl triphenylphosphonium bromide (26.8 g, 0.075 mol) in dry THF (60 mL) was added potassium tert-butoxide (7.6 g, 0.068 mol) at 0° C. After 30 minutes, the solution became canary yellow color, to that aldehyde S-I (5.1 g, 0.022 mol) in THF (30 mL) was added and allowed to stirred at 0° C. for 1 h. The reaction was quenched with brine (30 ml) and extracted with ethyl acetate (2×50 mL). Combined organic layer was washed with water (30 mL), brine (30 mL), dried over $Na_2SO_4$, filtered and concentrated in vacuo. Purification by column chromatography (silica gel 100-200, 0.5:9.5 ethyl acetate:petroleum ether) afforded S-II (4.2 g, 84%) as light brown oil. $^1H$ NMR (400 MHz, $CDCl_3$) δ=5.86 (dd, J. 11.0 Hz, 18.3 Hz, 1H), 5.65-5.53 (m, 2H), 5.06-5.05 (m, 1H), 5.03-5.02 (m, 1H), 4.15-4.09 (q, 2H), 2.48-2.39 (m, 2H), 2.23-2.18 (m, 1H), 2.12-2.07 (m, 1H), 1.82-1.73 (m, 2H), 1.25 (t, J. 7.3 Hz, 3H), 1.02 (s, 3H), 0.87 (d, J=6.4 Hz, 3H); $^{13}C$ NMR (100 MHz, $CDCl_3$) δ=173.7, 145.2, 128.6, 126.2, 113.3, 60.4, 41.2, 40.5, 36.7, 34.4, 31.5, 18.8, 16.4, 14.4. HRMS (ESI) calcd for $C_{14}H_{22}O_2Na^+$ 245.1512, found 245.1508.

1d) Synthesis of 2-((1R,5R,6S)-5,6-Dimethyl-6-vinylcyclohex-2-en-1-yl) acetaldehyde (S-III)

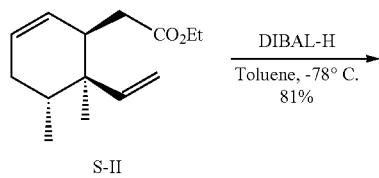

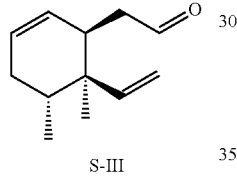

To a solution of ester S-II (0.5 g, 2.27 mmol) in dry distilled toluene (15 mL) was added DIBAL (1.0 M in toluene, 1.36 mL, 1.36 mmol) at −78° C. dropwise. Stirred at this temperature for 10 min and then added DIBAL (1.0 M in toluene, 1.13 mL, 1.13 mmol) at −78° C. dropwise. After stirring at the same temperature for 0.5 h, the reaction was quenched with methanol (3 mL), diluted with $Et_2O$ (20 mL) and sat. Na/K tartrate (15 mL). The solution was stirred at 25° C. for 2 h. Extracted the solution with ethyl acetate (3×20 mL), and the combined extracts were dried over $Na_2SO_4$. The crude mixture was passed through small bed of silica gel and eluted with 20% ethyl acetate:petroleum ether. The eluent was concentrated in vacuo to give the aldehyde S-III (0.33 g, 81%) as a colorless oil which is immediately used for next step.

1e) Synthesis of (3R,4S,5R)-3-allyl-4,5-dimethyl-4-vinylcyclohex-1-ene (6)

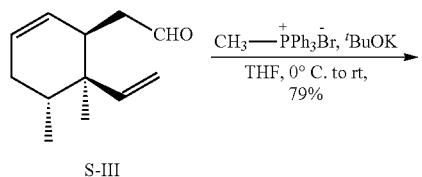

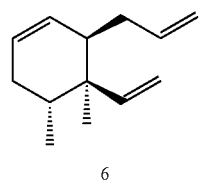

To a suspension of methyl triphenylphosphonium bromide (14.5 g, 0.040 mol) in dry THF (40 mL) was added potassium tert-butoxide (4.1 g, 0.037 mol) at 0° C. After 30 minutes, the solution became canary yellow color, to that aldehyde S-III (2.2 g, 0.012 mol) in THF (20 mL) was added and allowed to stirred at 0° C. for 1 h. The reaction was quenched with $NH_4Cl$ (20 ml) and extracted with petroleum ether (2×60 mL). Combined organic layer was washed with water (20 mL), brine (20 mL), dried over $Na_2SO_4$, filtered and concentrated in vacuo. Purification by column chromatography (silica gel 100-200, petroleum ether) afforded 6 (1.7 g, 79%) as colorless oil. Spectral data was identical with that of above compound 6.

1f) Synthesis of (3aR, 4R, 7aR)-3a, 4-Dimethyl-3a, 4,5,7a-tetrahydro-1H-indene (7)

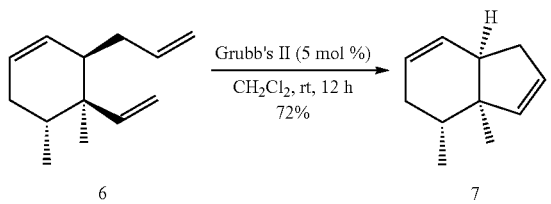

To a solution of 6 (2.0 g, 0.011 mol) in dry $CH_2Cl_2$ (100 mL) was added Grubbs' second-generation catalyst (480 mg, 5 mol %) at 25° C. After stirring for 24 h, reaction mixture was filtered through celite and filtrate was concentrated in vacuo. The crude material obtained after the removal of solvent was purified by column chromatography (silica gel 100-200, petroleum ether) to afford 7 (1.2 g, 72%) as colorless oil. $^1H$ NMR (400 MHz, $CDCl_3$) δ 5.79-5.72 (m, 2H), 5.69-5.66 (m, 2H), 2.56-2.49 (m, 1H), 2.25-2.20 (m, 1H), 2.11-2.04 (m, 1H), 1.93-1.87 (m, 1H), 1.78-1.69 (m, 1H), 1.63-1.56 (m, 1H), 0.92 (s, 3H), 0.90 (d, J=6.6 Hz, 3H); $^{13}C$ NMR (100 MHz, $CDCl_3$) δ 141.7, 129.3, 128.5, 125.9, 48.0, 47.7, 38.9, 34.1, 31.05, 18.7, 15.8;

1g) Synthesis of (3aR,4R)-3a, 4-dimethyl-1,6-dioxo-3a, 4,5,6-tetrahydro-1H-inden-2-ylium (8a)

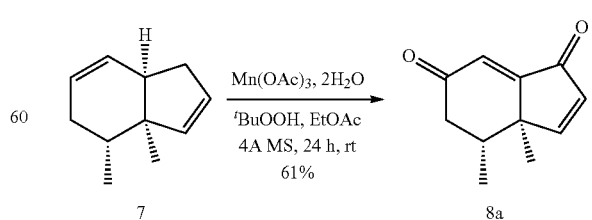

To a solution of diene 7 (1 g, 6.75 mmol) in EtOAc (100 mL) were added 4 Å molecular sieves (2 g) and $^tBuOOH$ (5.0 M in decane, 6.7 mL, 33.7 mmol) at room temperature. The reaction mixture was stirred for 30 min before Mn(OAc)$_3$.2H$_2$O (905 mg, 3.37 mmol) was added at 25° C. The resulting mixture was stirred at room temperature (25-30° C.) an under nitrogen atmosphere for 24 h before it was filtered through celite, eluted with EtOAc (30 mL) and concentrated in vacuo. The crude material obtained after the removal of solvent was purified by column chromatography (silica gel 100-200, 2:8 ethyl acetate:petroleum ether) to afford 8a and mono oxidised mixture which was again oxidised using similar reaction condition to give the 9 (725 mg, 61%) as yellow solid. Mp: 70-72° C.; $^1$H NMR (400 MHz, CDCl$_3$) δ 7.70 (d, J=5.9 Hz, 1H), 6.35 (d, J=5.9 Hz, 1H), 6.27 (s, 1H), 2.50-2.46 (m, 2H), 2.27-2.21 (m, 1H), 1.22 (s, 3H), 1.13 (d, J=6.4 Hz, 3H); $^{13}$C NMR (100 MHz, CDCl$_3$) δ 199.7, 195.8, 165.0, 160.4, 133.6, 121.8, 46.5, 42.8, 36.3, 18.4, 15.0; HRMS (ESI) calcd for C$_{11}$H$_{13}$O$_2$ [M+H]$^+$ 177.0910, found 177.0909.

1h) Synthesis of (1aS,1bR,2R,6aR)-1,1,1b,2-Tetramethyl-1,1a,1b,2,3,6a-hexahydrocyclopropa[a]indene-4,6-dione (Nardoaristolone B)

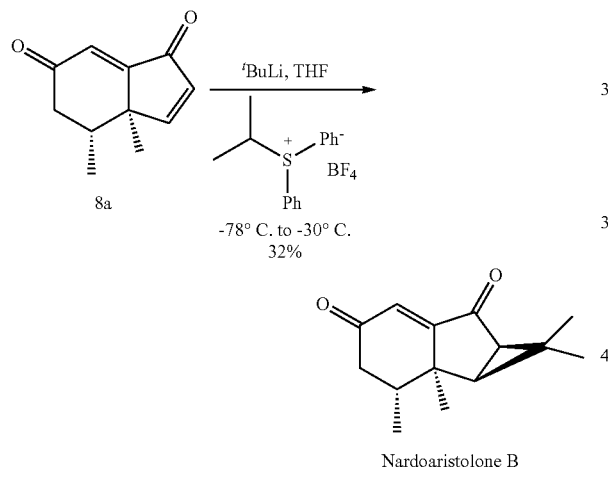

Nardoaristolone B

A 1.6 M solution of $^t$-BuLi in pentane (0.55 mL, 0.852 mmol) was added dropwise to a suspension of isopropyldiphenylsulfonium tetrafluoroborate (296 mg, 0.937 mmol) in THF (4 mL) at −78° C. After 30 min, 8a (50 mg, 0.284 mmol) was added as a solution in THF (2 mL). The resulting mixture was maintained at −30° C. for 1 h, quenched with saturated aqueous NH$_4$Cl (2 mL), and allowed to warm to 25° C. The reaction mixture was then extracted with ethyl acetate (3×5 mL). Combined organic layer was washed with water (5 mL), brine (5 mL), dried over Na$_2$SO$_4$, filtered and concentrated in vacuo. Purification by column chromatography (silica gel 100-200, 1.5:8.5 ethyl acetate:petroleum ether) afforded 1a Nardoaristolone B (20 mg, 32%) as yellow solid.

$^1$H NMR (400 MHz, CDCl$_3$) δ 6.18 (s, 1H), 2.40-2.23 (m, 3H), 1.94 (d, J=5.6 Hz, 1H), 1.77 (d, J=5.6 Hz, 1H), 1.17 (s, 3H), 1.13 (s, 3H), 1.09 (s, 3H), 1.06 (d, J=6.6 Hz, 3H); $^{13}$C NMR (100 MHz, CDCl$_3$) δ 201.5, 200.0, 165.1, 123.6, 44.3, 42.3, 42.2, 40.3, 35.5, 32.1, 28.8, 20.8, 17.8, 15.8; HRMS (ESI) calcd for C$_{14}$H$_{19}$O$_2$ [M+H]$^+$ 219.1380, found 219.1377.

Example 2

2a) Synthesis of (3aR,4R)-3a,4-Dimethyl-4,5,7,7a-tetrahydro-1H-indene-1,6(3aH)-dione (9)

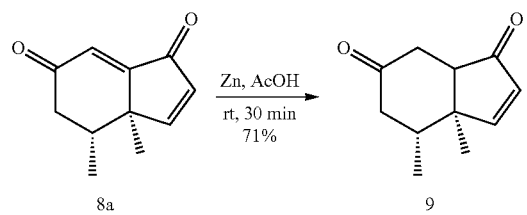

To a stirred solution of dienedione 8a (200 mg, 1.13 mmol) in CH$_3$COOH (10 mL) at 25° C. was added zinc dust (436 mg, 6.81 mmol). The resulting mixture was stirred for 30 min before being filtered on a short pad of Celite and washed with EtOAc (30 mL). The resulting organic layer was concentrated in vacuo and the crude obtained was purified on column chromatography (silica gel 100-200, 2.5:7.5 ethyl acetate:petroleum ether) to afford enone 9 (143 mg, 71%) as white solid. Mp: 68-70° C.

$^1$H NMR (400 MHz, CDCl$_3$) δ 7.75 (d, J=5.8 Hz, 1H), 6.17 (d, J=5.8 Hz, 1H), 2.67-2.62 (m, 1H), 2.53-2.48 (m, 1H), 2.32-2.26 (m, 2H), 2.20-2.14 (m, 1H), 2.07-2.04 (m, 1H), 1.16 (s, 3H), 1.07 (d, J=6.7 Hz, 3H); $^{13}$C NMR (100 MHz, CDCl$_3$) δ 210.0, 209.5, 170.5, 131.2, 51.5, 47.0, 43.1, 38.7, 35.1, 19.8, 15.5; HRMS (ESI) calcd for C$_{11}$H$_{14}$O$_2$Na$^+$ 201.0886, found 201.0885.

2b) Synthesis of (7R,7aR)-7,7a-Dimethyl-3a,6,7,7a-tetrahydrospiro[indene-5,2'-[1,3]dioxolan]-3(4H)-one (10)

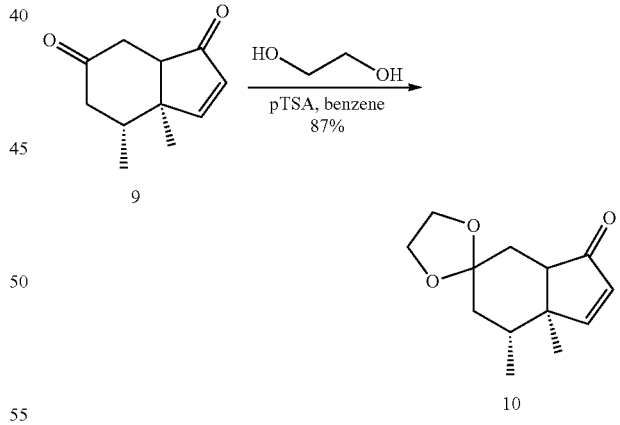

To a solution of the 9 (120 mg, 0.674 mmol) in benzene (10 mL) was added ethylene glycol (86 mg, 1.34 mmol) and pTSA (12 mg, 0.067 mmol) at room temperature. The reaction was reflux (80-85° C.) for 1 h then quenched by saturated NaHCO$_3$ (3 ml) and extracted with ethyl acetate (3×5 mL). Combined organic layer was washed with water (5 mL), brine (5 mL), dried over Na$_2$SO$_4$, filtered and concentrated in vacuo. Purification by column chromatography (silica gel 100-200, 2.0:8.0 ethyl acetate:petroleum ether) afforded 10 (130 mg, 87%) as white solid; Mp: 62-64° C. $^1$H NMR (400 MHz, CDCl$_3$) δ 7.65 (d, J=5.8 Hz, 1H), 6.07 (d, J=5.8 Hz, 1H), 3.98-3.87 (m, 4H), 2.21-2.12 (m, 2H), 1.81-1.77 (m, 1H), 1.74-1.70 (m, 1H), 1.66-1.56 (m, 2H), 1.15 (s, 3H), 0.96 (d, J=6.7 Hz, 3H); $^{13}$C NMR (100 MHz, CDCl$_3$) δ 209.4, 171.1, 130.5, 108.8, 64.4, 64.1, 54.6, 46.6, 39.5, 37.3, 30.1, 18.0, 16.4; HRMS (ESI) calcd for C$_{13}$H$_{18}$O$_3$Na$^+$ 245.1148, found 245.1143.

2c) Synthesis of (1aR,1bR,2R,6aS)-1,1,1b,2-Tetramethyloctahydro-6H-spiro[cyclopropa[a]indene-4,2'-[1,3]dioxolan]-6-one (11)

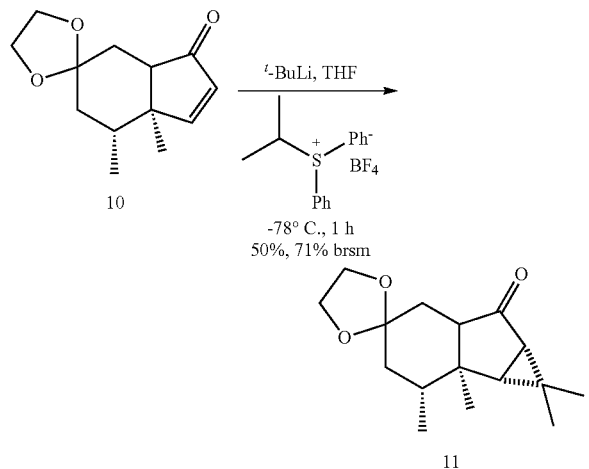

A 1.6 M solution of $^t$-BuLi in pentane (0.84 mL, 1.34 mmol) was added dropwise to a suspension of isopropyldiphenylsulfonium tetrafluoroborate (465 mg, 1.47 mmol) in THF (6 mL) at −78° C. After 30 min, 10 (100 mg, 0.446 mmol) was added as a solution in THF (4 mL). The resulting mixture was maintained at −20° C. for 1 h, quenched with saturated aqueous NH$_4$Cl (2 mL), and allowed to warm to 25° C. The reaction mixture was then extracted with ethyl acetate (3×10 mL). Combined organic layer was washed with water (10 mL), brine (10 mL), dried over Na$_2$SO$_4$, filtered and concentrated in vacuo. Purification by column chromatography (silica gel 100-200, 1.5:8.5 ethyl acetate: petroleum ether) afforded 11 (59 mg, 50%, 71% brsm) as white solid. $^1$H NMR (400 MHz, CDCl$_3$) δ 3.99-3.83 (m, 4H), Hz, 1H), 2.32-2.28 (m, 1H), 2.19-2.17 (m, 1H), 1.94-1.89 (m, 1H), 1.76 (d, J=5.8 Hz, 1H), 1.68 (d, J=5.8 Hz, 1H), 1.50-1.42, (m, 3H), 1.34 (s, 3H), 1.12 (s, 3H), 1.09 (s, 3H), 0.97 (d, J=6.8 Hz, 3H); $^{13}$C NMR (100 MHz, CDCl$_3$) δ 211.8, 107.8, 64.3, 63.9, 53.4, 43.7, 40.5, 40.2, 38.7, 37.2, 29.9, 28.9, 28.2, 18.0, 16.9, 16.4; HRMS (ESI) calcd for C$_{16}$H$_{24}$O$_3$Na$^+$ 287.1618, found 287.1614.

2d) Synthesis of (1aR,1bR,2R,6aS)-1,1,1b,2-Tetramethyl-1,1a,1b,2,3,6a-hexahydro-cyclopropa[a]indene-4,6-dione (1a)

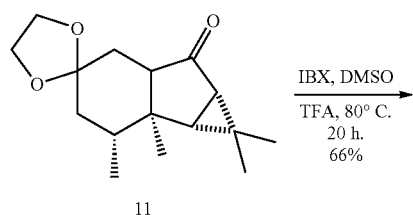

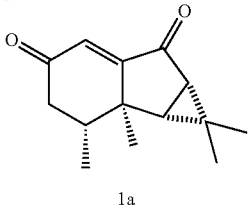

To a solution of ketone 11 (40 mg, 0.151 mmol) in DMSO (5 mL) were added IBX (128 mg, 0.454 mmol) and TFA (~1 drop) at 0° C. After being stirred at 80° C. for 24 h, the reaction mixture was quenched with saturated aqueous NaHCO$_3$ (2 mL). The aqueous layer was extracted with EtOAc (3×5 mL), the organic layer was washed with saturated aqueous NaHCO$_3$, water (10 mL), brine (10 mL), dried over Na$_2$SO$_4$, filtered and concentrated in vacuo. Purification by column chromatography (silica gel 100-200, 1.5:8.5 ethyl acetate:petroleum ether) afforded 12 (22 mg, 66%) as yellow solid. $^1$H NMR (400 MHz, CDCl$_3$) δ 6.12 (s, 1H), 2.46-2.31 (m, 2H), 2.19-2.14 (m, 1H), 2.01 (d, J=5.6 Hz, 1H), 1.94 (d, J=5.6 Hz, 1H), 1.33 (s, 3H), 1.23 (s, 3H), 1.22 (s, 3H), 1.15 (d, J=6.6 Hz, 3H); $^{13}$C NMR (100 MHz, CDCl$_3$) δ 201.6, 200.1, 165.0, 122.1, 42.5, 41.8, 41.5, 41.4, 40.0, 31.5, 29.1, 20.6, 16.4, 15.0; HRMS (ESI) calcd for C$_{14}$H$_{19}$O$_2$ [M+H]$^+$ 219.1380, found 219.1378.

Example 3

Synthesis of Ethyl(1R,1aS,1bR,2R,6aR)-1b,2-dimethyl-4,6-dioxo-1,1a,1b,2,3,4,6,6a-octahydrocyclopropa[a]indene-1-carboxylate (1b)

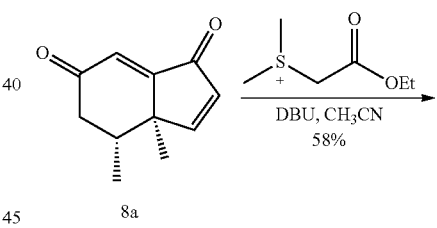

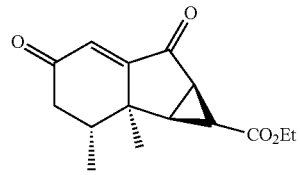

DBU (0.06 mL, 0.426 mmol) was added to a suspension of (ethoxycarbonylmethyl)-dimethylsulfonium bromide (97 mg, 0.426 mmol) in CHCl$_3$ (5.0 mL) at room temperature. After 30 min, compound 8a (50 mg, 0.284 mmol) in CHCl$_3$ (2.0 mL) was added and the solution was allowed to stir for 16 h at 25° C. The organic solvents were evaporated and then partitioned between CH$_2$Cl$_2$ (10 mL) and water (5 mL). The organic layer was washed with brine, dried over MgSO4, filtered, and concentrated. The residue was purified using silica gel chromatography (silica gel 100-200, 2.5:7.5 ethyl acetate:petroleum ether) afforded 1b (43 mg, 58%) as colorless oil. $^1$H NMR (400 MHz, CDCl$_3$) δ 6.22 (s, 1H), 4.09-4.02 (m, 2H), 2.52-2.48 (m, 1H), 2.42-2.31 (m, 4H), 2.28-2.24 (m, 1H), 1.26 (s, 3H), 1.19 (t, J=7.0 Hz, 3H), 1.15 (d, J=6.1 Hz, 3H); $^{13}$C NMR (100 MHz, CDCl$_3$) δ 199.9, 199.6, 168.8, 161.6, 124.2, 61.9, 43.5, 42.2, 35.4, 35.1, 31.5, 31.0, 21.3, 15.5, 14.0; HRMS (ESI) calcd for C$_{15}$H$_{18}$O$_4$Na$^+$ 285.1097, found 285.1094.

Example 4

Synthesis of (1aR,6aR)-1,1-Dimethyl-1a,1b,2,3,6, 6a-hexahydrocyclopropa[a]-inden-4(1H)-one (1c)

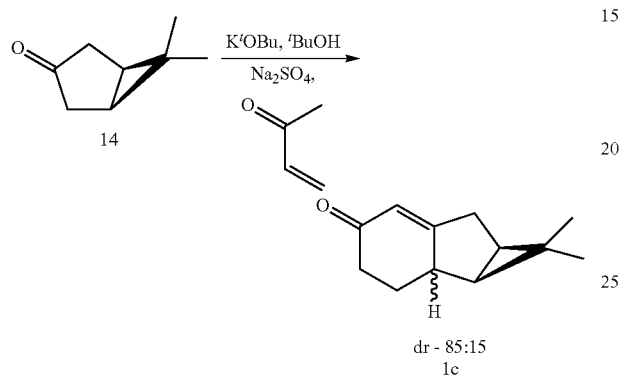

To a stirred solution of compound 14 (300 mg, 2.42 mmol) and Na$_2$SO$_4$ (1.5 g) in dry tert butanol (15 mL) at 25° C. was added catalytic amount of KO$^t$Bu (27 mg, 0.24 mmol) and then methyl vinyl ketone (0.25 mL, 2.90 mmol) slowly in drop wise manner. Stirring was continued for 30 min. Reaction was quenched by the addition of saturated aq.NH$_4$Cl (5 mL). Organic solvent was evaporated, water (10 mL) and ethyl acetate (15 mL) were added, organic solvent was separated and aqueous layer was extracted with ethyl acetate (3×10 mL), combined organic layer was washed with brine and dried over anhydrous Na$_2$SO$_4$. Purification by column chromatography (silica gel 100-200, 1.0:9.0 ethyl acetate:petroleum ether) afforded 1c (275 mg, 65%) as colourless oil. $^1$H NMR (400 MHz, CDCl$_3$) δ 5.69 (s, 1H), 2.70-2.63 (m, 1H), 2.45-2.34 (m, 3H), 2.30-2.25 (m, 1H), 2.21-2.17 (m, 1H), 2.03-1.98 (m, 1H), 1.82-1.73 (m, 1H), 1.33-1.29 (m, 1H), 1.04 (s, 3H), 0.99 (s, 3H); $^{13}$C NMR (100 MHz, CDCl$_3$) δ 199.5, 181.1, 120.8, 40.8, 37.8, 34.4, 32.3, 30.4, 29.0, 27.1, 22.8, 14.2. MS: 177.

Example 5

Synthesis of (1aR,6aR)-1,1,5-trimethyl-1a,1b,2,3,6, 6a hexahydrocyclopropa[a]inden-4(1H)-one (1d)

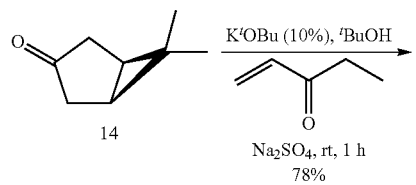

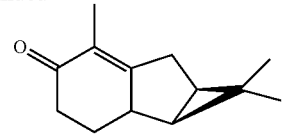

The compound 1d prepared by using similar procedure given in example 3.

$^1$H NMR (400 MHz, CDCl$_3$) δ 2.77-2.71 (m, 1H), 2.51-2.38 (m, 2H), 2.34-2.24 (m, 2H), 2.13-2.10 (m, 1H), 1.78-1.69 (m, 1H), 1.65 (m, 3H), 1.31-1.28 (m, 2H), 1.03 (s, 3H), 0.97 (s, 3H); $^{13}$C NMR (100 MHz, CDCl$_3$) δ 198.9, 174.2, 126.7, 41.4, 38.4, 34.9, 31.4, 30.3, 29.3, 27.2, 22.1, 14.3, 11.6.

Example: 6

Synthesis of (1aR,1bS,6aR)-1,1,2-Trimethyl-1a,1b, 2,3,6,6a-hexahydrocyclo propa[a]inden-4(1H)-one (1e)

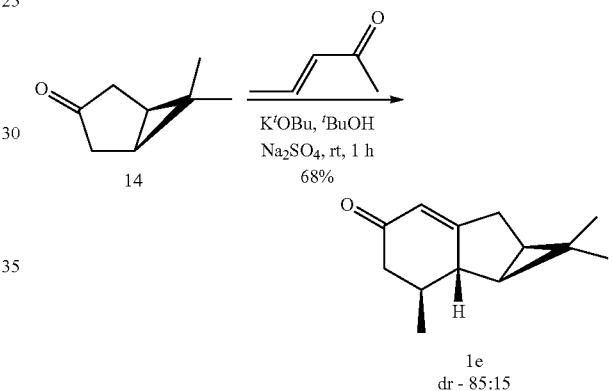

The compound 1d prepared by using similar procedure given in example 3.

IR (film) vmax 1667, 1373, 1236 cm$^{-1}$; $^1$H NMR (400 MHz, CDCl$_3$) δ 5.71 (s, 1H), 2.70-2.64 (m, 1H), 2.42-2.34 (m, 2H), 2.03-1.96 (m, 2H), 1.29-1.25 (m, 1H), 1.14-1.12 (m, 1H), 1.11 (d, J=5.9 Hz, 3H), 1.08-1.06 (m, 1H), 1.06 (s, 3H), 0.98 (s, 3H); $^{13}$C NMR (100 MHz, CDCl$_3$) δ 200.0, 180.3, 121.2, 48.1, 46.3, 37.0, 32.8, 32.3, 28.6, 27.2, 22.8, 20.7, 14.4; HRMS (ESI) calcd for C$_{13}$H$_{19}$O [M+H]$^+$ 191.1430, found 191.1429.

Example 7

Synthesis of (1aR,1bS,6aR)-2-Ethyl-1,1-dimethyl-1a,1b,2,3,6,6a hexahydrocyclo propa[a]inden-4 (1H)-one (1f)

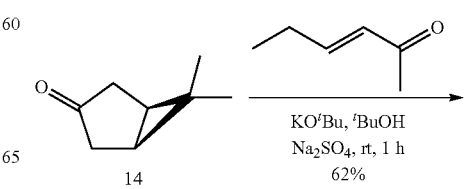

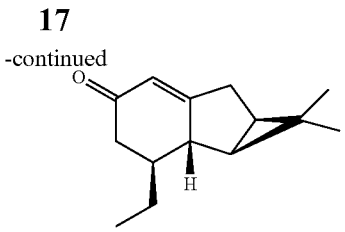

1f
dr - 85:15

The compound 1d prepared by using similar procedure given in example 3.

IR (film) vmax 1668, 1368, 1248 cm$^{-1}$; $^1$H NMR (400 MHz, CDCl$_3$) δ 5.71 (s, 1H), 2.70-2.64 (m, 1H), 2.53-2.49 (m, 1H), 2.38-2.34 (m, 1H), 2.11-2.08 (m, 1H), 1.97-1.90 (m, 1H), 1.87-1.82 (m, 1H), 1.77-1.71 (m, 1H), 1.36-1.25 (m, 2H), 1.15-1.13 (m, 1H), 1.06 (s, 3H), 0.98 (s, 3H), 0.92 (t, J=7.3 Hz, 3H); $^{13}$C NMR (100 MHz, CDCl$_3$) δ 200.2, 180.6, 121.0, 46.1, 43.1, 42.8, 32.7, 32.3, 28.7, 27.4, 27.3, 22.9, 14.4, 10.6; HRMS (ESI) calcd for C$_{14}$H$_{21}$O [M+H]$^+$ 205.1587, found 205.1584.

Example 8

Synthesis of (1aR,1bS,6aR)-1,1-Dimethyl-2-propyl-1a,1b,2,3,6,6a-hexahydrocyclo propa[a]inden-4(1H)-one (1g)

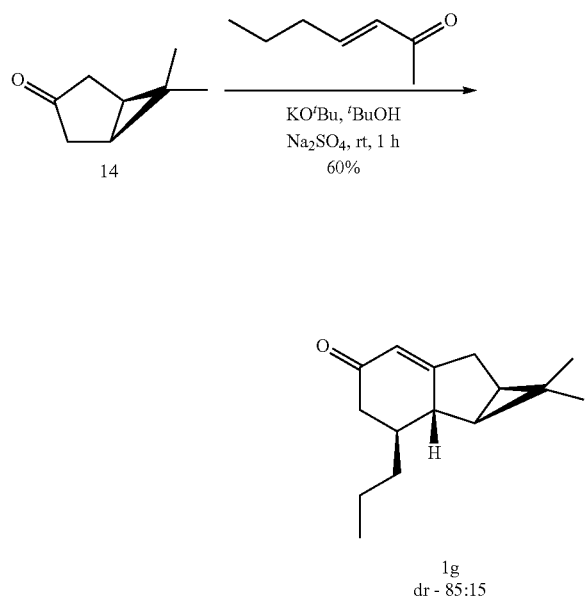

1g
dr - 85:15

IR(film) vmax 1669, 1351, 1233 cm$^{-1}$; $^1$H NMR (400 MHz, CDCl$_3$) δ 5.67 (s, 1H), 2.65-2.60 (m, 1H), 2.49-2.47 (m, 1H), 2.35-2.30 (m, 1H), 2.17-2.10 (m, 1H), 2.06-2.04 (m, 1H), 1.91-1.86 (m, 2H), 1.63-1.59 (m, 1H), 1.43-1.35 (m, 1H), 1.25-1.19 (m, 2H), 1.12-1.10 (m, 1H), 1.03 (s, 3H), 0.95 (s, 3H), 0.89 (t, J=7.3 Hz, 3H); $^{13}$C NMR (100 MHz, CDCl$_3$) δ 200.1, 180.5, 121.0, 46.5, 43.4, 41.5, 37.2, 32.8, 32.3, 28.6, 27.3, 22.9, 19.4, 14.4, 14.3; HRMS (ESI) calcd for C$_{15}$H$_{23}$O [M+H]$^+$ 219.1743, found 219.1739.

Example 9

Synthesis of (1aR,1bR,6aR)-1,1,2,2-Tetramethyl-1a,1b,2,3,6,6a-hexahydro cyclo propa[a]inden-4(1H)-one (1h)

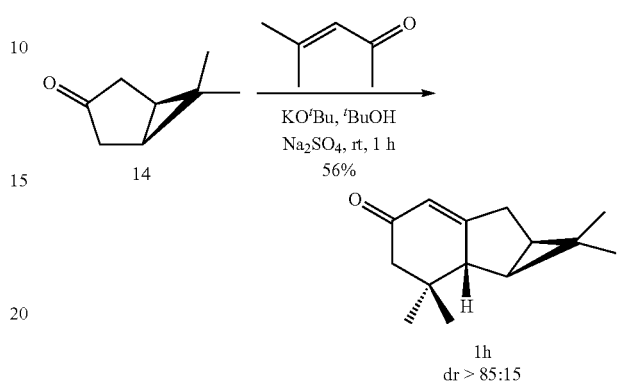

1h
dr > 85:15

IR (film) vmax 1668, 1367, 1246 cm$^{-1}$; $^1$H NMR (400 MHz, CDCl$_3$) δ 5.78 (s, 1H), 2.71-2.64 (m, 1H), 2.44-2.36 (m, 2H), 2.18 (s, 2H), 1.28-1.26 (m, 1H), 1.13 (s, 3H), 1.11-1.09 (m, 1H), 1.07 (s, 3H), 0.97 (s, 3H), 0.91 (s, 3H); $^{13}$C NMR (100 MHz, CDCl$_3$) δ 199.7, 178.3, 121.4, 53.1, 51.6, 38.5, 32.6, 30.4, 30.0, 28.7, 27.3, 21.8, 19.9, 14.3; HRMS (ESI) calcd for C$_{14}$H$_{21}$O [M+H]$^+$ 205.1587, found 205.1583.

Example 10

Protocol Adopted for the Mosquito Repellence Bioassay Methodology

Mosquito repellence activity was assessed on the basis of protection period (hr) offered by various analogues of Nootkatone against Mosquito bites. The protection period was measured on the basis of the concept "time until the first bite" pioneered by Granette (Comparison of mosquito repellency test under laboratory and field conditions. Granett, P. *Proc Ann Meet NJ Mosq Assoc,* 1938, vol. 25, 51,). Repellence tests were carried out against 3-5 days old, blood starved but sucrose fed (0.5M solution), *Ae. aegypti* females mosquitoes, drawn from well-established laboratory colony maintained at 27±1° C. Temperatureand 70±5% Relative humidity. The light intensity was regulated at 300-500 lux for testing against laboratory, colonized Ae. *aegypti*, a day biting mosquito. Human volunteer's hand covered with polythene disposable gloves was introduced in the cage containing about 200 hungry mosquitoes. Mosquitoes were allowed to bite on the back of the hand through muslin screen stuck over a small window (2 cm×2 cm) cutout in the polythene bag. Various analogues of Nootkatone were loaded on the muslin cloth screen instead of direct skin application so as to avoid the potential risk involved in the evaluation of natural products of unknown mammalian toxicity. All the test solutions were made in Analar grade Acetone The muslin cloth screen was first treated with the analogue taking two doses @0.25 mg/cm$^2$ and 0.5 mg/cm$^2$ and the solvent was evaporated before use. Control muslin screen was treated with solvent alone. After introduction of the hand covered with the polythene glove with the treated muslin screen into the mosquito cage, number of mosquito bites received in subsequent 5 minutes were counted. In the event of no bites in the initial 5 minutes exposure, the test hand was exposed repeatedly after every consecutive ½ hr for 5 minutes test till the time a confirmed bite was received. Number of hours before the receipt of a confirmed bite (Techniques for the evaluation of insect repellents. A critical review (Schreck, C. E, *Ann Rev Entomol,* 1977, vol 22, 101) represented the protection period offered by the test compound. In control rate of mosquito bite was 10-12 bites/min. Above test were repeated with both male and female human volunteers using different mosquito batches. All the tests were carried out at 27±1° C. temperature between 9.00-17.00 hrs.

Protection Time Offered by Nardoaristolone and its Various Analogues

| Sample | Protection period in hrs @dose 0.25 mg/cm$^2$ | Protection period in hrs @dose 0.50 mg/cm$^2$ |
| --- | --- | --- |
| Recemic nardoaristolone B | 3.30 ± 0.0708 | 5.63 ± 0.1778 |
| 1a | 4.13 ± 0.0626 | 5.35 ± 0.0868 |
| 1b | 1.23 ± 0.040 | 1.40 ± 0.0549 |
| 1c | 3.60 ± 0.0791 | 5.30 ± 0.088 |
| 1d | 5.64 ± 0.1984 | 6.29 ± 0.0844 |
| 1e | 5.22 ± 0.0720 | 6.46 ± 0.1507 |
| 1f | 1.53 ± 0.1223 | 3.48 ± 0.1396 |
| 1g | 1.8 ± 0.1490 | 1.99 ± 0.11366 |
| 1h | 2.19 ± 0.0716 | 2.38 ± 0.07567 |
| Recemic nootkatone | 3.12 ± 0.07 | 5.06 ± 0.06 |
| Natural nootkatone | 5.58 ± 0.171 | >7 hrs |

ADVANTAGES OF THE INVENTION

Compounds possess improved efficacy,
Simple processes for synthesis of natural compounds provided

We claim:
1. A compound of formula (I)

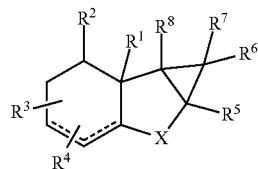

Formula (I)

wherein
$R^1$, $R^3$, and $R^4$ are selected from the group consisting of hydrogen, alkyl ($C_1$ to $C_2$), COOH, COR, CONRR, $CH_2OR$, and NRR;
$R^2$, $R^6$, $R^7$ and $R^8$ are selected from group consisting of hydrogen, alkyl ($C_1$ to $C_4$), COOH, COR, CONRR, $CH_2OR$, NRR;
$R^5$ is selected from group consisting of hydrogen, COOH, CONRR, $CH_2OR$, and NRR;
wherein any two of $R^1$, $R^2$, $R^3$, $R^4$, $R^5$, $R^6$, $R^7$, $R^8$ may form a 3 to 8 membered carbocyclic ring which may optionally be substituted or may contain a heteroatom selected from O or N;
X is selected from C=O; C=S or C—R—R;
R is hydrogen;
'........' represents a single or double bond;
either of the rings in formula (I) may additionally contain at least one carbonyl group or salt thereof.

2. The compound as claimed in claim 1, wherein the compounds of formula (I) are selected from the group consisting of:
i. (1aR,1bR,2R,6aS)-1,1,1b,2-Tetramethyl-1,1a,1b,2,3,6a-hexahydro-cyclopropa[a]indene-4,6-dione (1a),
ii. Ethyl(1R,1aS,1bR,2R,6aR)-1b,2-dimethyl-4,6-dioxo-1,1a,1b,2,3,4,6,6a-octahydrocyclopropa[a]indene-1-carboxylate (1b),
iii. (1aR,6aR)-1,1-Dimethyl-1a,1b,2,3,6,6a-hexahydrocyclopropa[a]-inden-4(1H)-one (1c),
iv. (1aR,6aR)-1,1,5-trimethyl-1a,1b,2,3,6,6a hexahydro-cyclopropa[a]inden-4(1H)-one (1d),
v. (1aR,1bS,6aR)-1,1,2-Trimethyl-1a,1b,2,3,6,6a-hexahydrocyclo propa[a]inden-4(1H)-one (1e),
vi. (1aR,1bS,6aR)-2-Ethyl-1,1-dimethyl-1a,1b,2,3,6,6a-hexahydrocyclopropa[a]inden-4(1H)-one (1f),
vii. (1aR,1bS,6aR)-1,1-Dimethyl-2-propyl-1a,1b,2,3,6,6a-hexahydrocyclopropa[a]inden-4(1H)-one (1g),
viii. (1aR,1bR,6aR)-1,1,2,2-Tetramethyl-1a,1b,2,3,6,6a-hexahydrocyclopropa[a]inden-4(1H)-one (1h).

3. A process for the preparation of compounds of formula (I) as claimed in claim 1, wherein said process comprising the steps of:
a) adding boron trifluoride diethyl etherate ($BF_3.OEt_2$) to a solution of diene compounds of formula 4

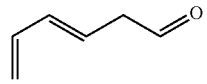

4 and (E)-2-methylbut-2-enal of formula 3

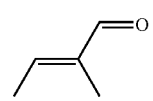

3 in Dichloromethane ($CH_2Cl_2$) followed by stirring the reaction for the period ranging from 10 to 12 h at temperature in the range of −78° C. to 30° C. to afford compound of formula 6

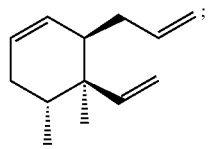

or b) adding Grubbs second-generation catalyst to a solution of compound of formula 6 of step (a) followed by stirring the mixture for 22 to 24 h temperature in the range of 25 to 30° C. to afford compound of formula 7

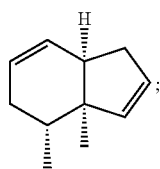

7 c) adding Manganese triacetate dehydrate [Mn(OAC)₃.2H₂O] and tert-butyl hydroperoxide (t-BuOOH) to a solution of compound of formula 7 of step (b) in ethyl acetate (EtOAc) followed by stirring the reaction mixture for 22 to 24 h at temperature 25 to 30° C. to give compound of formula 8a

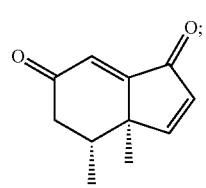

8a d) adding 1,8-Diazabicyclo[5.4.0]undec-7-ene (DBU) to a suspension of (ethoxycarbonylmethyl)-dimethylsulfonium bromide in chloroform (CHCl₃) to obtain a mixture followed by addition of solution of compound of formula 8a of step (c) in CHCl₃ and stirring the reaction mixture to afford compound of formula 1b

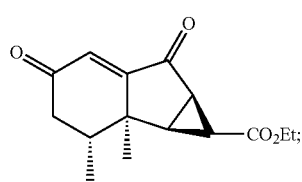

1b e) adding zinc dust to a stirred solution of dienedione of formula 8a of step (c) in acetic acid followed by stirring for 20 to 30 min at temperature in the range of 25 to 30° C. to afford enone compound of formula 9

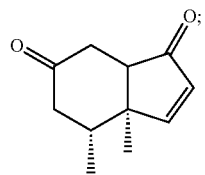

9 f) adding ethylene glycol and p-Toluenesulfonic acid (PTSA) to a solution of compound of formula 9 of step (e) in benzene followed by refluxing for 50 to 60 minutes at temperature in the range of 80 to 85° C. to afford compound of formula 10

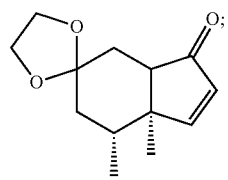

10 g) adding the solution of ᵗ-BuLi in pentane and isopropyldiphenylsulfonium tetrafluoroborate in THF to a solution of compound of formula 10 of step (f) followed by cooling the reaction mixture to (−)15 to (−)20° C. for 50 to 60 minutes quenching the reaction mixture to give compound of formula 11

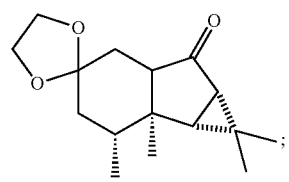

11 h) adding 2-iodoxybenzoic acid (IBX) and trifluoroacetic acid (TFA) to a solution of ketone of formula 11 of step (f) in dimethyl sulfoxide (DMSO) followed by stirring the reaction mixture at 70 to 80° C. for 20 to 24 h to afford compound of formula (I).

4. The process for the preparation of compounds of formula (I) as claimed in claim 3, wherein the step (c) is carried out under nitrogen atmosphere.

5. The process for the preparation of compounds of formula (I) as claimed in claim 3, wherein the process further comprises adding a solution of tert-Butyllithium (ᵗ-BuLi) in pentane and isopropyldiphenylsulfonium tetrafluoroborate in THF to a solution of compound of formula 8a

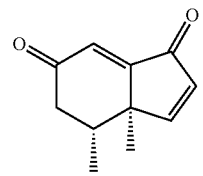

8a of step (c) followed by cooling the mixture to −30° C. for 1 h to afford Nardoaristolone B

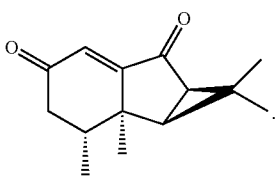

Nardoaristolone B

6. A process for the preparation of compounds of formula (I) as claimed in claim 1, wherein said process comprises adding potassium tert-butoxide (KOtBu) and ketone compound to a stirred solution of compound of formula 14 ((1R,5S)-6,6-dimethylbicyclo[3.1.0]hexan-3-one)

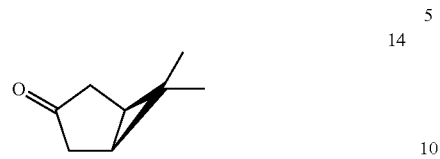

14 and sodium sulfate (Na$_2$SO$_4$) in tertiary butanol followed by stirring the reaction mixture for the period ranging from 0.5 h-6 h at temperature 25° C.-60° C. to afford compounds of formula (I).

7. The process for the preparation of compounds of formula (I) as claimed in claim 6, wherein ketone compounds is selected from methyl vinyl ketone, pent-1-en-3-one, (E)-pent-3-en-2-one, (E)-hex-3-en-2-one, (E)-hept-3-en-2-one, 4-methylpent-3-en-2-one.

8. The compound as claimed in claim 1, wherein the compounds are used as insect repellents.

9. The compound as claimed in claim 1, wherein protection period of the compounds of formula (I) against mosquito bites is in the range of 1.23 h to 6.46 h at the concentration in the range of 0.25 to 0.50 mg/cm$^2$.

\* \* \* \* \*